US012090267B2

United States Patent
Pellegrini et al.

(10) Patent No.: US 12,090,267 B2
(45) Date of Patent: Sep. 17, 2024

(54) AEROSOL-GENERATING APPARATUS INCLUDING SELF-DIAGNOSTICS

(71) Applicant: PHILIP MORRIS PRODUCTS S.A., Neuchâtel (CH)

(72) Inventors: Fabian Pellegrini, Cortaillod (CH); Fabrice Steffen, Colombier (CH); Eric Mariacher, Jougne (FR)

(73) Assignee: Philip Morris Products S.A., Neuchâtel (CH)

( * ) Notice: Subject to any disclaimer, the term of this patent is extended or adjusted under 35 U.S.C. 154(b) by 922 days.

(21) Appl. No.: 17/055,982

(22) PCT Filed: May 14, 2019

(86) PCT No.: PCT/IB2019/053997
§ 371 (c)(1),
(2) Date: Nov. 16, 2020

(87) PCT Pub. No.: WO2019/220348
PCT Pub. Date: Nov. 21, 2019

(65) Prior Publication Data
US 2021/0212378 A1    Jul. 15, 2021

(30) Foreign Application Priority Data
May 18, 2018    (EP) .................................... 18173344

(51) Int. Cl.
*A24F 40/20* (2020.01)
*A24F 40/46* (2020.01)
(Continued)

(52) U.S. Cl.
CPC ........... *A61M 11/042* (2014.02); *A24F 40/46* (2020.01); *A24F 40/53* (2020.01); *A24F 40/60* (2020.01);
(Continued)

(58) Field of Classification Search
CPC .......... A24F 40/53; A24F 40/65; A24F 40/90; A24F 40/46; A24F 40/60; A24F 40/20; A24F 40/95; G08B 5/38; A61M 11/042
(Continued)

(56) References Cited

U.S. PATENT DOCUMENTS 9,609,895 B2 * 4/2017 Galloway ............... A24F 40/50
9,770,055 B2 * 9/2017 Cameron ................ A24F 40/30
(Continued)

FOREIGN PATENT DOCUMENTS

CN          106666834 A    5/2017
JP          2012-527222 A  11/2012
(Continued)

OTHER PUBLICATIONS

Extended EP Search Report for EP Application No. 18173344.5 issued by the European Patent Office on Nov. 21, 2018; 8 pgs.
(Continued)

*Primary Examiner* — Abdullah A Riyami
*Assistant Examiner* — Vladimir Imas
(74) *Attorney, Agent, or Firm* — Mueting Raasch Group

(57) ABSTRACT

Aerosol-generating apparatus (100) for self-diagnosis allow users to initiate the self-diagnostics and then provide a diagnostic indication using, for example, indicators (162). The aerosol-generating apparatus (100) may include an aerosol-generating device (102) and a host device (101). The host device (101) may include one or more user-selectable switches (152) to initiate a self-diagnostic procedure and one or more indicators (162) to depict or display the diagnostic indication.

29 Claims, 4 Drawing Sheets

Figure 1:
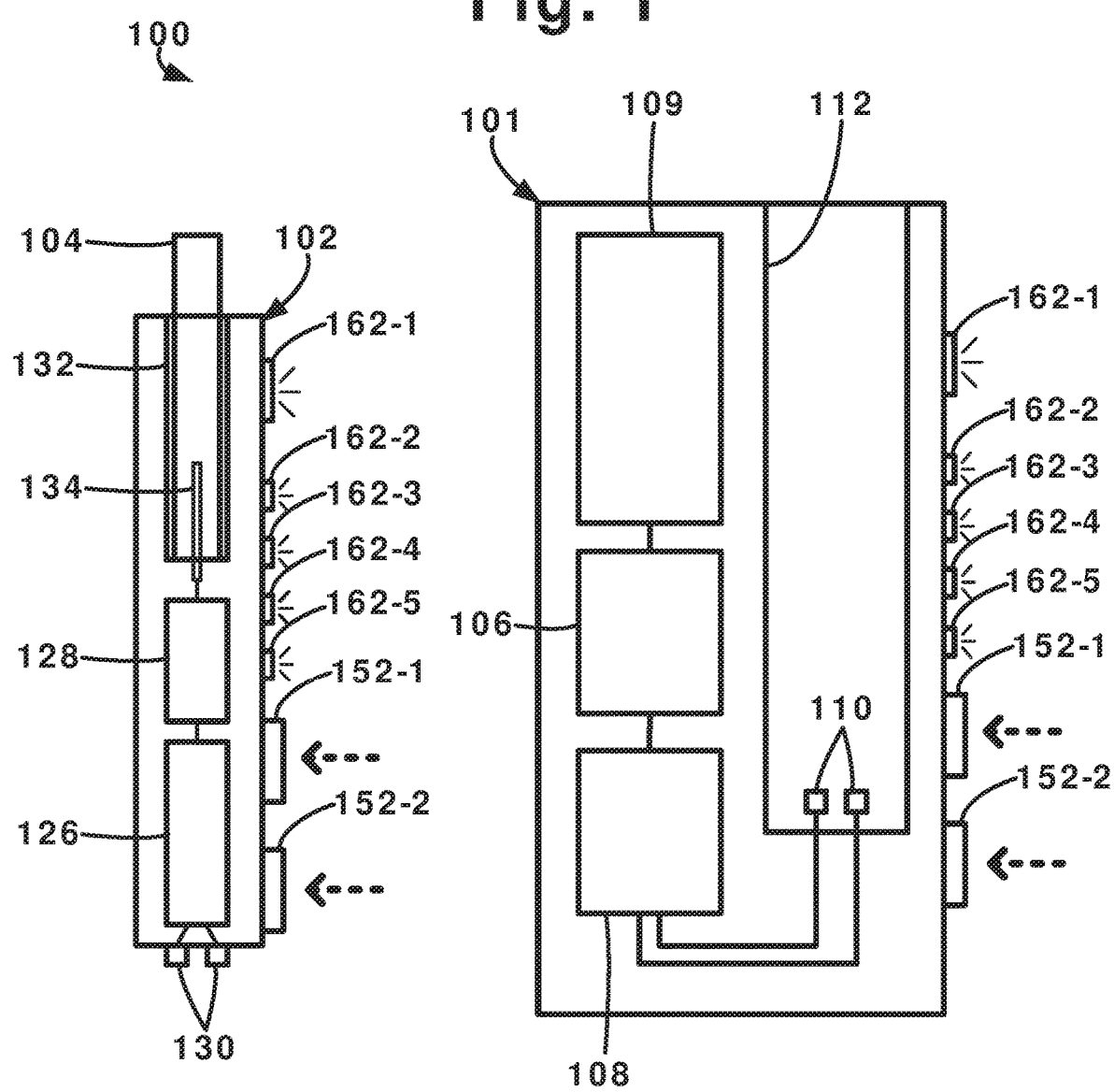

(51) Int. Cl.
  *A24F 40/53* (2020.01)
  *A24F 40/60* (2020.01)
  *A24F 40/65* (2020.01)
  *A24F 40/90* (2020.01)
  *A24F 40/95* (2020.01)
  *A61M 11/04* (2006.01)
  *G08B 5/38* (2006.01)

(52) U.S. Cl.
  CPC .............. *A24F 40/65* (2020.01); *A24F 40/90* (2020.01); *A24F 40/95* (2020.01); *G08B 5/38* (2013.01); *A24F 40/20* (2020.01)

(58) Field of Classification Search
  USPC ......................................................... 131/328
  See application file for complete search history.

(56) References Cited

U.S. PATENT DOCUMENTS

| | | | | |
|---|---|---|---|---|
| 9,913,497 | B2* | 3/2018 | Galloway | ............... A24F 40/80 |
| 2003/0197512 | A1 | 10/2003 | Miller et al. | |
| 2018/0020727 | A1 | 1/2018 | Hoffman et al. | |
| 2018/0093054 | A1 | 4/2018 | Bowen et al. | |
| 2020/0281276 | A1* | 9/2020 | Akao | ...................... A24F 40/51 |
| 2020/0352249 | A1* | 11/2020 | Achtien | ............ A61M 15/0066 |
| 2021/0007406 | A1* | 1/2021 | Bessant | ................... A24F 40/50 |
| 2021/0315280 | A1* | 10/2021 | Alarcon | ............... G06Q 30/016 |
| 2022/0022554 | A1* | 1/2022 | Jain | ........................ A24F 40/65 |

FOREIGN PATENT DOCUMENTS

| | | |
|---|---|---|
| JP | 2017-514463 A | 6/2017 |
| JP | 2017-127300 A | 7/2017 |
| RU | 2627004 C2 | 8/2017 |
| RU | 2640176 C2 | 12/2017 |
| RU | 2647805 C2 | 3/2018 |
| WO | WO 2010/133342 A A | 11/2010 |
| WO | WO 2013/116567 A1 | 8/2013 |
| WO | WO 2014/150247 A1 | 9/2014 |
| WO | WO 2014/150773 A1 | 9/2014 |
| WO | WO 2015/165747 A1 | 11/2015 |
| WO | WO 2017/001520 A | 1/2017 |
| WO | WO 2017/055801 A1 | 4/2017 |

OTHER PUBLICATIONS

International Search Report and Written Opinion for PCT/IB2019/053997, issued by the European Patent Office on Sep. 13, 2019; 14 pgs.

International Preliminary Report on Patentability for PCT/IB2019/053997, issued by the European Patent Office on Aug. 18, 2020; 8 pgs.

Japanese Office Action for JP Application No. 2020-563945 issued by the Japanese Patent Office on Jul. 3, 2023; 15 pgs. Including English translation.

Russian Office Action issued for RU 2020141696 by the Patent Office of the Russian Federation on Sep. 6, 2022; 17 pgs. including English translation.

* cited by examiner

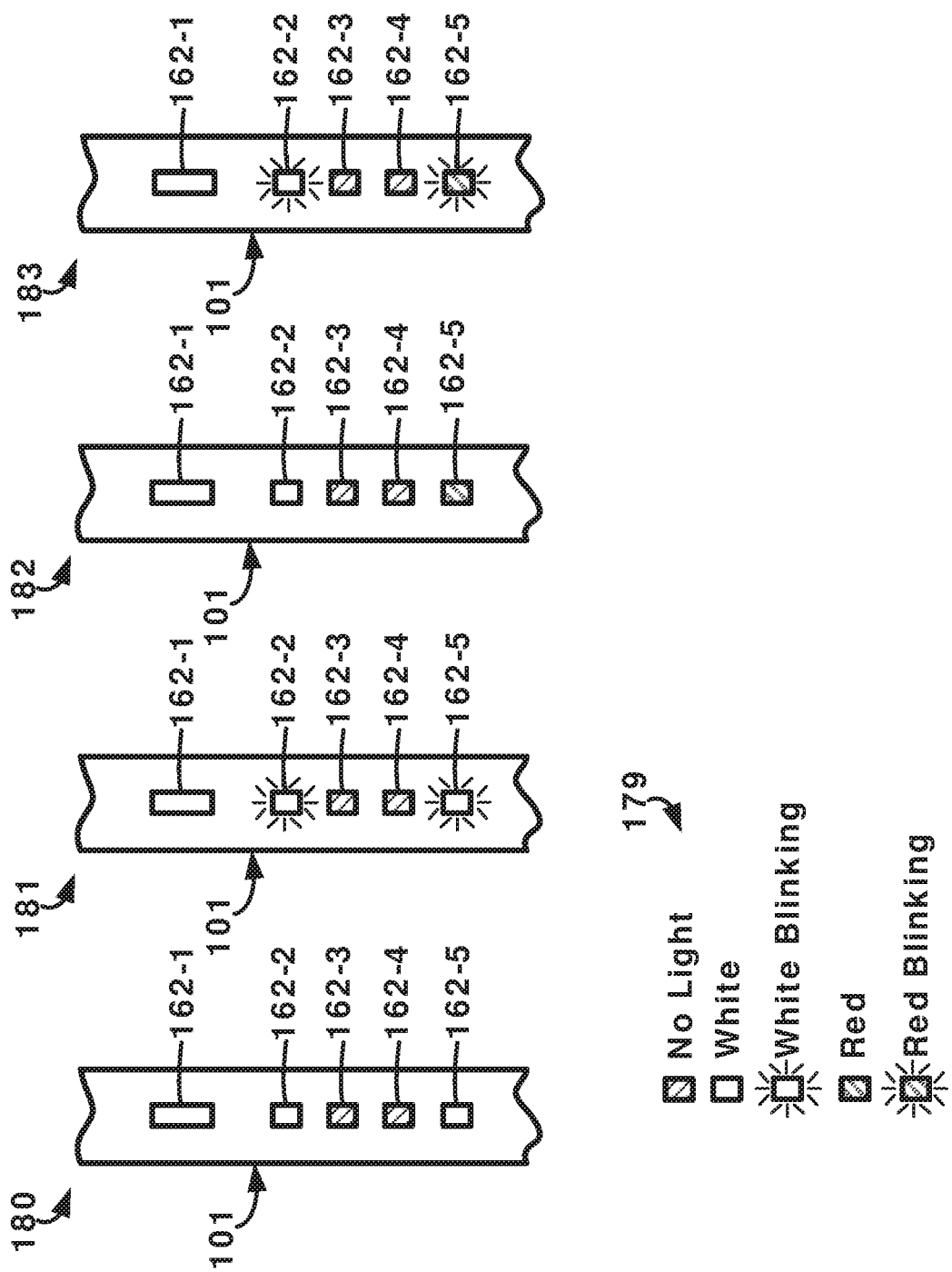

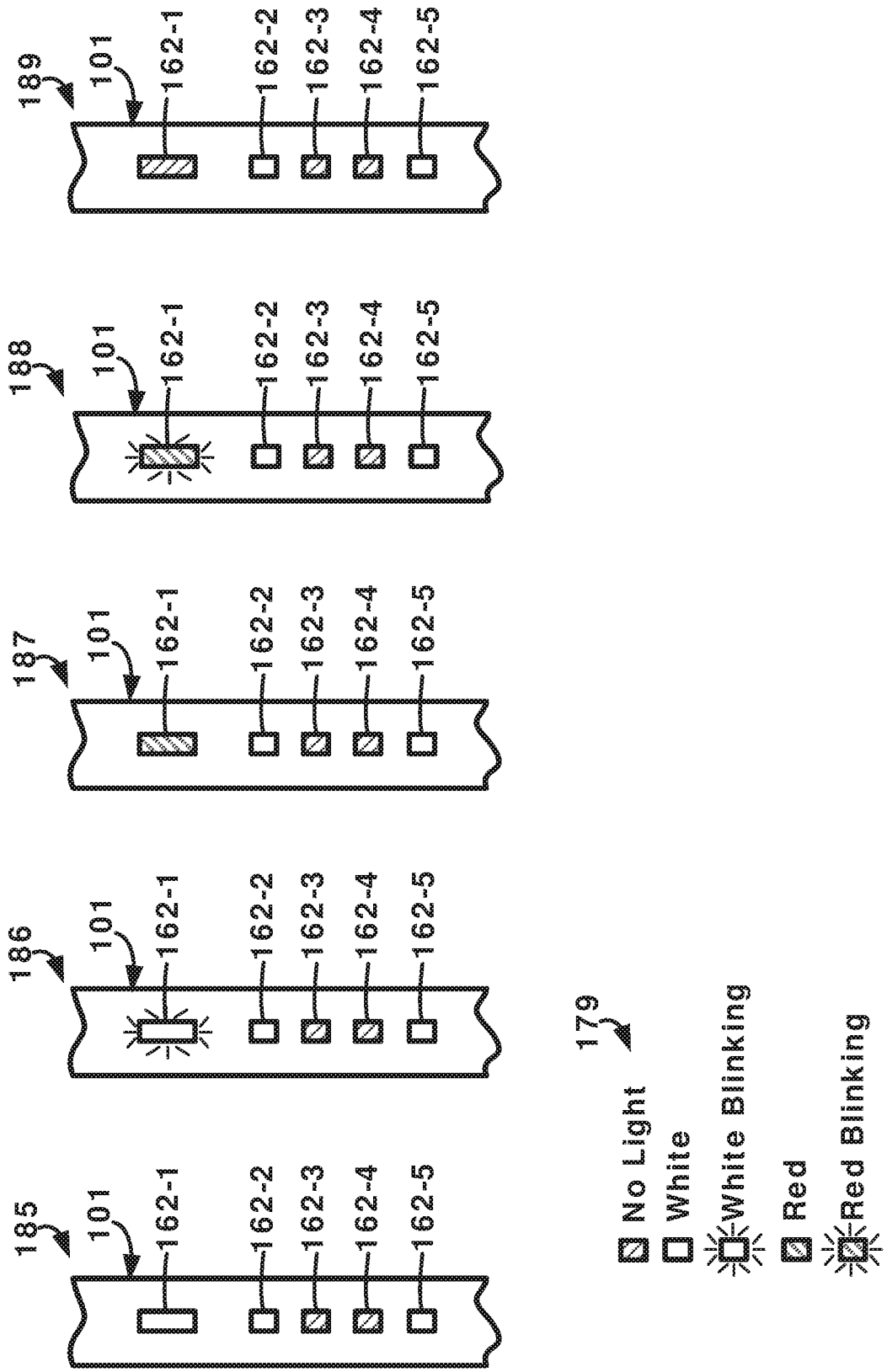

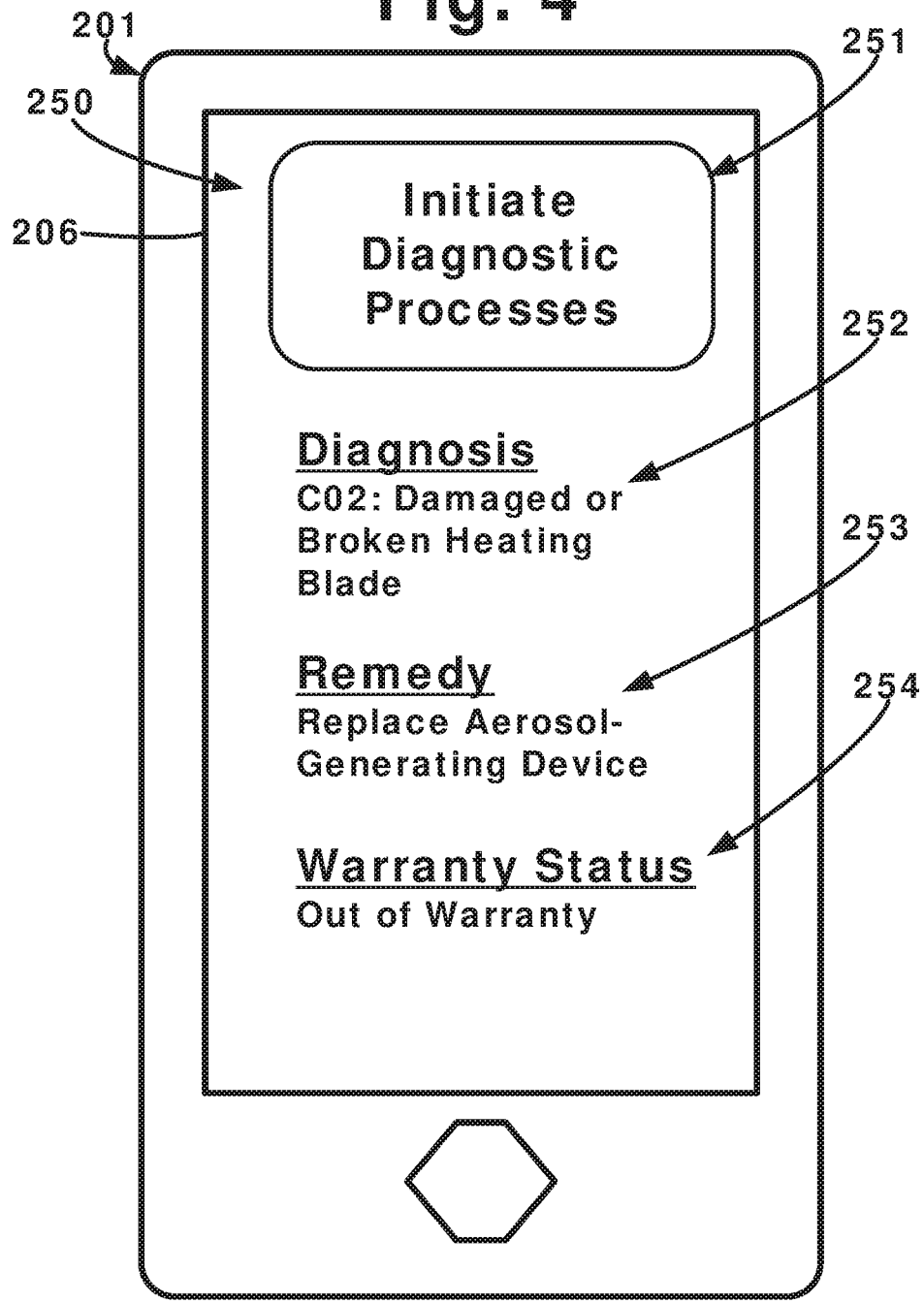

AEROSOL-GENERATING APPARATUS INCLUDING SELF-DIAGNOSTICS

This application is the § 371 U.S. National Stage of International Application No. PCT/IB2019/053997, filed 14 May 2019, which claims the benefit of European Application No. 18173344.5, filed 18 May 2018, the disclosures of which are incorporated by reference herein in their entireties.

This invention relates to systems, apparatus, devices, computer program products, and methods for use in self-diagnostics, or self-diagnostic processes, of aerosol-generating apparatus. The diagnostics may be initiated by a user, the self-diagnostics may be performed, and then a diagnostic indication may be displayed to the user indicating the results of the self-diagnostics.

Aerosol-generating apparatus may malfunction due to a variety of different reasons and users may be required to take or send their malfunctioning aerosol-generating apparatus to a shop or servicer to determine the malfunction as well as a potential remedy for the malfunction. In other words, nowadays to run a diagnostic for aerosol-generating apparatus, users may need to go to a "Point of Sale" to have their aerosol-generating apparatus checked. Such users may wish to avoid the time-consuming processes of taking or sending their malfunctioning aerosol-generating apparatus to a shop or servicer.

Additionally, some aerosol-generating apparatus malfunctions may be more easily remedied than others. For example, some aerosol-generating apparatus malfunctions may simply be due to user error, which may be quickly and easily corrected through one or both of verbal instruction and visual demonstration. Once the malfunction is determined, users may wish to remedy the malfunction themselves or with the assistance of another without the time-consuming processes of taking or sending their malfunctioning aerosol-generating apparatus to a shop or servicer.

Further, sometimes, aerosol-generating apparatus may malfunction within or outside of a warranty time period, within which certain repairs may be covered by a manufacturer. Users may wish to determine whether their aerosol-generating apparatus is within or outside of a warranty time period to, for example, help the user decide whether to purchase a new aerosol-generating apparatus or work with the manufacturer to repair or replace their aerosol-generating apparatus that is under warranty.

Still further, warranty status of aerosol-generating apparatus may be based on various criteria that may not be conveniently or practically tracked by a user. For instance, a warranty of aerosol-generating apparatus may be based on usage data such as, for example, amount of puffs or inhalations, number of aerosol-generating articles used, amount of charges or charge cycles of a host device, amount of charges or charge cycles of an aerosol-generating device, time from purchase, time from manufacture, and time since last service. Such usage data may not be readily available to a user. Further, the requirements of the warranty may also not be readily or easily understandable by a user.

Additionally, aerosol-generating apparatus may include various diagnostic processes that are not able to be initiated by a user. Instead, such various diagnostic processes may only be performed by shops or servicers that include one or both of specialized equipment and specialized knowledge.

Yet still further, aerosol-generating apparatus including, for example, aerosol-generating devices for use in generating aerosol using aerosol-generating articles and host devices for use in, among other things, charging aerosol-generating devices may be relatively small so as to be easily carried by users. The small size of the aerosol-generating apparatus may force the aerosol-generating apparatus to include a limited amount of display devices and input devices and may limit the size of the battery. Thus, the small size of the aerosol-generating apparatus may make it challenging for users to obtain data such as self-diagnostic data or warranty data from the aerosol-generating apparatus. Further, larger display devices or more display devices may require more power, which could limit the amount of use between charges for aerosol-generating apparatus, especially when the size of the battery is limited.

More specifically, aerosol-generating apparatus may need to be very physically small. For example, the aerosol-generating apparatus may be similar in size to only a portion of a conventional cigarette to give a similar sensation to a conventional cigarette in order to gain wide acceptance by smokers of conventional combustible cigarettes. Further, for example, the aerosol-generating apparatus may be a smaller size simply for convenience of users carrying the aerosol-generating apparatus. Therefore, the hardware on which software can be embedded needs to be very compact and this provides very limited space for a user interface or display devices. Usually, there is space for no more user interface features than one or more user-selectable switches (for example, depressible buttons, non-depressible buttons such as contact or capacitive switches, etc.) and one or more indicators (for example, lights such as light emitting diode (LED), liquid crystal displays, etc.).

Thus, the processes following malfunction of aerosol-generating apparatus may be problematic and challenging for users. For example, it may be inconvenient, time-consuming, cumbersome, and problematic for users to take or send their aerosol-generating apparatus to a shop or servicer, especially when the remedy is something that the user may perform, or execute, themselves. Additionally, a diagnosis and subsequent remedy, or fix, may not be timely if leaving the malfunctioning aerosol-generating apparatus with a servicer or sending the malfunctioning aerosol-generating apparatus to a servicer. Further, for example, warranty information may not be readily available or easily discernible by a user.

Still further, for example, users may not have the specialized equipment nor knowledge needed to perform diagnostics of their aerosol-generating apparatus. Lastly, aerosol-generating apparatus may not include many display devices or large display devices so as to provide self-diagnostic data or warranty information. Additionally, a limited amount of input devices may also make it challenging for users to perform, or execute, any self-diagnostics that may be available. Also, larger displays, for example, may consume too much power.

One object of examples of the invention is to provide users a fast, easy, and convenient way to initiate self-diagnostics, or self-diagnostic processes, of their aerosol-generating apparatus without, for example, taking or sending their aerosol-generating apparatus to a servicer or shop. Another object to the examples of the invention is to provide one or more simple diagnostic indications to user based on self-diagnostic procedures such that a user may quickly and easily discern what the self-diagnostic procedures have determined about their malfunctioning aerosol-generating apparatus. Additionally, another object to the examples of the invention is to provide warranty information to a user in an easily discernible way. As such, users may be able to self-remedy some malfunctions or problems such as, for example, a reversable user error, or users may be able to have additional diagnostic information at their disposal so as to be able to make an informed decision whether to repair or replace their aerosol-generating apparatus.

Another object of examples of the invention is to allow intuitive and easy ways for users to initiate self-diagnostics, or self-diagnostic processes, of their aerosol-generating apparatus using the limited number of user-selectable switches that are part of the aerosol-generating apparatus and discern the results of the self-diagnostics, or self-diagnostic processes, using the limited number of indicators that are part of the aerosol-generating apparatus.

In one aspect there is provided a method for use with an aerosol-generating apparatus comprising allowing a user to initiate diagnostics of an aerosol-generating apparatus, performing a self-diagnostic procedure of the aerosol-generating apparatus in response to initiation of diagnostics of aerosol-generating apparatus by the user, and providing a diagnostic indication to the user based on at least the self-diagnostic procedure.

The computerized method addresses the technical or technological problem particular to implementation on a computer that is specific to this technological environment. Computers are good at carrying out some tasks, but poor at other tasks. The technical solution disclosed considers tasks that general-purpose computers are good at performing self-diagnostic procedures and providing diagnostic indications to users based on at least the self-diagnostic procedure. The method, system, computer program and computer program product described significantly help users in diagnosing malfunctions of their aerosol-generating apparatus.

In one aspect there is provided a computer program product comprising a non-transitory computer readable medium having program code portions stored thereon, the program code portions configured, when said program product is run on a computer, to: allow a user to initiate diagnostics of an aerosol-generating apparatus, perform a self-diagnostic procedure of the aerosol-generating apparatus in response to initiation of diagnostics of aerosol-generating apparatus by the user, and provide a diagnostic indication to the user based on at the least self-diagnostic procedure.

In one aspect there is provided an apparatus a controller comprising one or more processors and the controller is configured to: allow a user to initiate diagnostics. The controller is further configured to perform a self-diagnostic procedure of the aerosol-generating apparatus in response to initiation of diagnostics by the user and provide a diagnostic indication to the user based on at least the self-diagnostic procedure.

The aerosol-generating apparatus preferably includes an aerosol-generating device configured to use an aerosol generating article to generate aerosol. The aerosol-generating device includes a power supply to, for example, provide power to the aerosol-generating device for use in the generation of aerosol using aerosol-generating articles. Also, the aerosol-generating apparatus preferably includes a host device comprises an interface to be operably coupled to the aerosol-generating device to at least recharge the power supply of the aerosol-generating device.

One or both of the aerosol-generating device and the host device may include a controller and one or more user-selectable switches to allow the user to initiate diagnostics. Preferably, the diagnostics—the self-diagnostic procedures—may be performed, or executed, when the aerosol-generating device is operably coupled to the host device. Each of aerosol-generating device and the host device may include a communication interface to send and receive data to each other as well as other devices such as, for example, a user interface device.

In other embodiments, the diagnostics—the self-diagnostic procedures—may be performed, or executed, when the aerosol-generating device is not operably coupled to the host device. For instance, one or both of the aerosol-generating device and the host device may perform the diagnostics—the self-diagnostic procedures—on themselves when they are apart from each other.

Additionally, in another embodiment, the diagnostics may be initiated using a user interface device that is operably coupled to one or both of the aerosol-generating device and the host device using a communication interface.

Various aspects of the systems, devices, and methods according to the present invention may provide one or more advantages relative to currently-available aerosol-generating apparatus and associated systems. For example, currently-available aerosol-generating apparatus and associated systems may not include easy and intuitive user-initiated, self-diagnostics. The self-diagnostics of the illustrative aerosol-generating apparatus is advantageous because they provide a fast, convenient, and reliable process, or method, to provide diagnostic data, without taking or sending the aerosol-generating apparatus to a servicer or shop.

The present invention relates to methods, processes, computer products, apparatus, and systems for self-diagnostics of aerosol-generating apparatus. More specifically, the illustrative methods, processes, computer products, apparatus, and systems may be used by a user that would like to diagnose a problem with their aerosol-generating apparatus. The user may initiate a self-diagnostic procedure, and then be provided a diagnostic indication regarding the results of the self-diagnostic procedure.

It may be further described that the present invention is directed to providing aerosol-generating apparatus, or a smoking device, with a means for running a diagnostic analysis which may be enabled by a user interface specifically arranged on the device itself. In this way, advantageously, the user may run the diagnostic independently without having to go to a "point of sale." More practically, a user, in case of any problems related to the device, may contact a call center and, via phone, an operator may inform him/her about a procedure for enabling the self-diagnostic procedure.

According to a preferred embodiment, the chosen way to run the diagnostic analysis may be in the rapid (for example, within two seconds) consecutive activation (for example, five times) of one of the buttons located on the aerosol-generating apparatus. After the diagnostic is run, the aerosol-generating apparatus may show a feedback in terms of result. For example, a blinking light of a first color may yield a first result, while a blinking light of a second color may yield a second result, different from the first result.

Thus, the present invention may be described as being a simple diagnostic tool using the existing user interface (for example, LEDs) in order to quickly and accurately identify device malfunctioning for determining replacement policy. In one embodiment, a user may enter the aerosol-generating apparatus into diagnostic mode by selecting (for example, touching, clicking etc.) a user-selectable switch (for example, a Bluetooth button) a selected number of times (for example, five times) within a selected period of time (for example, two seconds). The aerosol-generating apparatus may then perform the self-diagnostic procedure and then display a diagnostic indicator reflective of the results of the self-diagnostic procedure.

The aerosol-generating device may define a cavity for receiving the aerosol-generating article and may include a heater configured to heat the aerosol-generating substrate of the article to generate aerosol. The heater may include a blade that is configured to be inserted into an aerosol-generating article to deliver heat to the aerosol-generating substrate of the article. The aerosol-generating device may include a power supply to at least power the heater and may be configured to be interfaced, or operatively coupled, to a host device. The host device may include an interface to be interfaced, or operably coupled, to the aerosol-generating device to at least charge the power supply of the aerosol-generating device.

One or both of the aerosol-generating device and host device may include a controller comprising one or more processors and a communication interface to transfer data to and from each other and other devices such as a user interface device. Preferably, the aerosol-generating device and the host device may communicate using a data coupling (for example, each may include at least one data interface port for communication of data that may be mated to each other) when the aerosol-generating device is received by the host device. Further, for example, a wireless communication interface such as a BLUETOOTH wireless protocol interface may be used between the aerosol-generating device and the host device. The controller may include one or more processors (for example, microprocessors) that may operate with associated data storage, or memory, for access to processing programs or routines and one or more types of data that may be employed to carry out the illustrative methods. For example, processing programs or routines stored in data storage may include programs or routines for performing self-diagnostics, statistics, matrix mathematics, compression algorithms (for example, data compression algorithms), standardization algorithms, comparison algorithms, or any other processing used to implement the one or more illustrative methods and processes described herein. Further, for example, processing programs or routines stored in data storage may include processes and functions to perform self-diagnostic procedures of the aerosol-generating device and the host device, transfer data and commands between the aerosol-generating device and host device, and wirelessly transfer data and commands between the aerosol-generating device, the host device, and a user interface device. The data storage, or memory, may be further configured to store diagnostic data and related routines, and any other data and/or formulas necessary to perform the processes and methods described herein.

In one or more embodiments, the aerosol-generating device and host device may be described as being implemented using one or more computer programs executed on one or more programmable processors that include processing capabilities (for example, microcontrollers, programmable logic devices, etc.), data storage (for example, volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The computer program products used to implement the processes described herein may be provided using any programmable language, for example, a high-level procedural and/or object orientated programming language that is suitable for communicating with a computer system. Any such program products may, for example, be stored on any suitable device, for example, a storage media, readable by a general or special purpose program, controller apparatus for configuring and operating the computer when the suitable device is read for performing the procedures described herein. In other words, at least in one embodiment, the user interface device may be implemented using a non-transitory computer readable storage medium, configured with a computer program, where the storage medium so configured causes the computer to operate in a specific and predefined manner to perform functions described herein.

The exact configuration of the controller of the aerosol-generating device and host device is not limiting and essentially any device capable of providing suitable computing capabilities and control capabilities to implement the illustrative methods described herein may be used. In view of the above, it will be readily apparent that the functionality as described in one or more embodiments according to the present invention may be implemented in any manner as would be known to one skilled in the art. As such, the computer language, the controller, or any other software/hardware which is to be used to implement the processes described herein shall not be limiting on the scope of the systems, processes or programs (for example, the functionality provided by such processes or programs) described herein. The methods and processes described in this disclosure, including those attributed to the apparatus, or various constituent components, may be implemented, at least in part, in hardware, software, firmware, or any combination thereof. For example, various aspects of the techniques may be implemented within one or more processors, including one or more microprocessors, DSPs, ASICs, FPGAs, CPLDs, microcontrollers, or any other equivalent integrated or discrete logic circuitry, as well as any combinations of such components. When implemented in software, the functionality ascribed to the systems, devices, and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The term "controller" and "processor" refers to any device or apparatus capable of providing suitable computing capabilities and control capabilities such as, for example, microprocessors, digital signal processors (DSP), application specific integrated circuits (ASIC), field-programmable gate arrays (FPGA), equivalent discrete or integrated logic circuitry, or any combination thereof and of providing suitable data storage capabilities that includes any medium (for example, volatile or non-volatile memory, a CD-ROM, magnetic recordable medium such as a disk or tape, etc.) containing digital bits (for example, encoded in binary, trinary, etc.) that may be readable and/or writeable.

The term "communication interface" refers to any device or apparatus capable of providing suitable data communication capabilities between an aerosol-generating device, a host device, and a user interface device such as, for example, physical data couplings (for example, each may include at least one data interface port for communication of data that may be mated to each other when the aerosol-generating device is received by the host device), various telemetry circuits and antennas and may use one or more wired or wireless (for example, radio frequency) data transmission protocols such as, for example, BLUETOOTH, WI-FI, any protocol in the ultra-high frequency (UHF) band, any protocol in the super high frequency (SHF) band, low frequencies, or combinations thereof.

One or both of the aerosol-generating device and host device includes one or more user-selectable switches. The one or more user-selectable switches may be described as buttons configured to be selected by a user to perform, or initiate, one or more actions of the aerosol-generating device and host device. Preferably, the user-selectable switch comprises a depressible button. As used herein, a user may select a user-selectable switch by touching, clicking, tapping, or swiping the user-selectable switch with a body part such as, for example, a finger. At least one user-selectable switch may be used to allow the user to initiate diagnostics. For example, a user may use at least one user-selectable switch to initiate diagnostics such as the self-diagnostic procedures described herein. Preferably, only the host device includes one or more user-selectable switches to perform, or initiate, the self-diagnostics described herein.

As noted herein, the aerosol-generating device may be operably coupled to the host device, and when the aerosol-generating device is operably coupled to the host device, user selection of user-selectable switch of the host device may initiate self-diagnostics of one or both of the aerosol-generating device and the host device. In other ways, a user-selectable switch of the aerosol-generating device may be selected to initiate self-diagnostics of the aerosol-generating device, and a user-selectable switch of the host device may be selected to initiate self-diagnostics of the host device. Although the use of a single user-selectable switch for use by a user to initiate the diagnostics is described herein, it is to be understood that the invention may include the use of more than one, or two or more, user-selectable switches to initiate the to initiate self-diagnostics of the aerosol-generating apparatus.

The one or more user-selectable switches may also be multi-purpose. For example, the one or more user-selectable switches may perform various actions when selected by a user such as, for instance, powering on the device, initiating wireless connectivity, etc., and a selected pattern may be used by a user to initiate another action separate from the switches' primary action. More specifically, a user may perform selection of the user-selectable switch according to a selected pattern, which may trigger, or initiate, the self-diagnostic procedure or mode. The selected pattern may be a pattern that would not be normally triggered during typical use of the aerosol-generating apparatus. Further, the selected pattern may be a pattern that would not likely be accidentally triggered when the aerosol-generating apparatus is being carried in a user's pocket. In one example, the selected pattern may include a series of rapid selections of the user-selectable switch within a selected time period such as, for instance and preferably, five selections within two seconds. Additionally, once in the diagnostic mode, the aerosol-generating apparatus may be reset using a user-selectable switch (for example, selected or pressing two user-selectable switches) or by waiting two minutes for the aerosol-generating apparatus to exit the diagnostic mode automatically.

One or both of the aerosol-generating device and the host device may include one or more indicators to display the diagnostic indication to the user. Preferably, the one or more indicators include a plurality, or two or more, lights such as, for example, LEDs. The one or more indicators may be configured to emit light according one or more selected characteristics to provide the diagnostic indication when the aerosol-generating apparatus is configured in a diagnostic mode. For example, the one or more selected characteristics may include light color and light blinking. Thus, in one example, one or more indicators may blink a selected pattern and/or depict a selected color to display the diagnostic indication to the user. Preferably, only the host device includes one or more indicators to display the diagnostic indication to the user.

Further, a plurality of different patterns may be created using a few indicators that could be different colors or could blink, and each of the plurality of different patterns may correspond to a different diagnostic code that could be identified by a user. The diagnostic code may correspond to additional information with respect to the identified malfunction, which in some examples, may be used to remedy the malfunction.

Additionally, when the aerosol-generating apparatus is configured in a diagnostic mode, the indicators may further provide a diagnosis mode indication to the user to indicate that the aerosol-generating apparatus is configured in diagnosis mode in response to initiation of diagnostics of aerosol-generating apparatus by the user. In this way, a user may quickly and easily determine that the user successfully initiated the self-diagnostics, for example, using a selected pattern of selection of the user-selectable switch.

The diagnostic indication provided by the indicators to the user may be indicative of physical damage to the aerosol-generating apparatus. Physical damage to the aerosol-generating apparatus may include a broken heater blade of an aerosol-generating device of the aerosol-generating apparatus, damaged cavity of the host device, damage interface of one or both of the aerosol-generating device and host device, peeling paint, damaged door or latch spring, damaged lid, damaged button, damaged charging connecter of the host device (for example, USB connector damaged due to overheating, dust, pin damage, etc.), damaged display window, damaged or dirty contact points on the operably interface between the aerosol-generating apparatus and the host device, damage to the aerosol-generating article receiver of the aerosol-generating apparatus, damaged cap of the aerosol-generating apparatus, and damaged rear or middle housing of the aerosol-generating apparatus.

The diagnostic indication provided by the indicators to the user may further be indicative of software and electrical malfunctions of the aerosol-generating apparatus. Software and electrical malfunctions of the aerosol-generating apparatus may include malfunctioning indicator behavior (for example, various indicators may fail to "light up"), aging battery, device out of operating temperature range (range is 10 degrees Celsius to 60 degrees Celsius), malfunctioning charging behavior, wireless connectivity malfunction (for example, Bluetooth failure to connect), and no vibration. Further, the diagnostic indication provided by the indicators to the user may be indicative of improper usage of the aerosol-generating apparatus. For example, improper usage of the aerosol-generating apparatus may include errant insertion of the aerosol-generating device into the host device (for instance, the wrong end of the aerosol-generating device may be inserted into the host device).

The illustrative embodiments may further include determining whether the aerosol-generating apparatus is in a warranty period, and the diagnostic indication to the user may be indicative of whether the aerosol-generating apparatus should be replaced and is within or outside of the warranty period. For example, if the aerosol-generating apparatus is determined to be malfunctioning, need of replacement, and within the warranty period, the diagnostic indication may indicate to the user that the aerosol-generating apparatus should be replaced and is likely covered by warranty (because, for example, it occurred within the warranty time period). Further, for example, if the aerosol-generating apparatus is determined to be malfunctioning, need of replacement, and outside of the warranty period, the diagnostic indication may indicate to the user that the aerosol-generating apparatus should be replaced but is not covered by warranty (because, for example, it occurred outside of the warranty time period).

The aerosol-generating apparatus may be further configured to interoperate with a user interface device that is separate from the aerosol-generating apparatus. The user interface device may include a controller, communication interface, and a graphical user interface that may be interacted with to initiate the self-diagnostics of the aerosol-generating apparatus. The controller and communication interface of the user interface device may be similar to that of the aerosol-generating apparatus and the host described herein.

The user interface device may provide a graphical region (for example, a graphical button) on the graphical user interface that a user may select to initiate the self-diagnostics. Upon selection, the user interface device may wirelessly communicate with the aerosol-generating apparatus via a communication interface to send a self-diagnostic initiation command. After the self-diagnostic procedure has been completed by the aerosol-generating apparatus, the aerosol-generating apparatus may transmit diagnostic data, or information, back to the user interface device, and the user interface device may display the diagnostic indication on the graphical user interface.

Preferably, the user interface device is a cellular telephone. Generally, the user interface device may be described as any electronic device including a display for providing a graphical user interface capable of being interacted with by a user. The user interface device includes a communication interface such as, for example, at least a telemetry circuit and an antenna, for bidirectional communication with other devices such as aerosol-generating apparatus, servers, network devices, personal computers, and the like and with other networks such as the internet and the like. More specifically, data and commands may be transmitted and received during uplink or downlink telemetry between the user interface device, aerosol-generating apparatus, and other devices and/or networks using the communication interface. In at least one embodiment, the communication interface is a wireless interface using one or more wireless (for example, radio frequency) data transmission protocols such as, for example, BLUETOOTH, WI-FI, any protocol in the ultra-high frequency (UHF) band, any protocol in the super high frequency (SHF) band, low frequencies, etc.

The user interface device may further include a display operatively coupled the controller for the output of data via the display. The display may be further configured to depict and be used as a user interactable, graphical user interface. The graphical user interface and display may comprise a touchscreen. The graphical user interface may be described as being user interactable because the graphical user interface may be configured to allow a user to view and/or manipulate data on the display, to allow a user to interact with user interface device, and the like.

The graphical user interface may be configured to allow a user to select a graphical region to send a diagnostic initiation message from the user interface device to the aerosol-generating apparatus. The diagnostic initiation message may trigger the aerosol-generating apparatus to execute, or perform, the self-diagnostic procedure. The aerosol-generating apparatus may provide the diagnostic indication to the user interface device, and the diagnostic indication may be displayed to the user on a graphical user interface.

Preferably, the user interface device may be used in conjunction with an illustrative aerosol-generating apparatus. The aerosol-generating apparatus may include an aerosol-generating device and a host device. The term "aerosol-generating device" refers to a device configured to use, or utilize, an aerosol-generating article that releases volatile compounds to form an aerosol that may be inhaled by a user. The term "aerosol-generating article" refers to an article that comprises a substrate capable of releasing, upon heating, volatile compounds, which may form an aerosol. The aerosols generated from aerosol-generating articles according to the invention may be visible or invisible and may include vapours (for example, fine particles of substances, which are in a gaseous state, that are ordinarily liquid or solid at room temperature) as well as gases and liquid droplets of condensed vapours. A "heated-type aerosol-generating article" is an aerosol-generating article that comprises an aerosol-generating substrate and is configured for use with an aerosol-generating device that is configured to heat, but not combust, the aerosol-generating substrate. One example of a heated-type aerosol-generating article are the IQOS heat sticks, also known as MARLBORO HEATSTICKS, from Phillip Morris International for use in an IQOS, heat not burn, aerosol-generating device, also from Phillip Morris International.

All scientific and technical terms used herein have meanings commonly used in the art unless otherwise specified. The definitions provided herein are to facilitate understanding of certain terms used frequently herein. As used herein, the singular forms "a", "an", and "the" encompass embodiments having plural referents, unless the content clearly dictates otherwise. As used herein, "or" is generally employed in its sense including "and/or" unless the content clearly dictates otherwise. The term "and/or" means one or all of the listed elements or a combination of any two or more of the listed elements. As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like. The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Reference will now be made to the drawings, which depict one or more aspects described in this disclosure. However, it will be understood that other aspects not depicted in the drawing fall within the scope and spirit of this disclosure. Like numbers used in the figures refer to like components, steps and the like. However, it will be understood that the use of a number to refer to a component in a given figure is not intended to limit the component in another figure labelled with the same number. In addition, the use of different numbers to refer to components in different figures is not intended to indicate that the different numbered components cannot be the same or similar to other numbered components.

FIG. 1 is a schematic sectional view of an illustrative aerosol-generating apparatus 100 including an aerosol-generating device 102 and a host device 101 configured to interface with the aerosol-generating device 102.

FIG. 2 are views of indicators 162 of the illustrative host device 101 of FIG. 1 for use in providing a diagnostic indication related to the self-diagnosis of the host device 101.

FIG. 3 are views of indicators 162 of the illustrative host device 101 of FIG. 1 for use in providing a diagnostic indication related to the self-diagnosis of the aerosol-generating device 102.

FIG. 4 is a schematic representation of an illustrative user interface device for use with self-diagnostics of aerosol-generating apparatus.

The schematic drawings are not necessarily to scale and are presented for purposes of illustration and not limitation.

An illustrative aerosol-generating apparatus 100 is depicted in FIG. 1. Preferably, the aerosol-generating apparatus 100 includes an aerosol-generating device 102 and a host device 101. The aerosol-generating device 102 comprises a cavity 132 for receiving a second type of aerosol-generating article such as a heat stick 104 and a heater 134, which is configured to provide a source of heat to the heat stick 104 thus producing inhalable aerosol. The aerosol-generating device 102 further includes a controller 128 comprising one or more processors and associated memory. The controller 128 may be associated with the heater 134 so as to, among other things, perform diagnostics with respect to the heater 134. The controller 128 may further include a communication interface such as, for example, a wireless communication interface to, for example, communicate with the host device 101 and a user interface device 201 shown in FIG. 4. The communication interface of the controller 128 may preferably comprise a BLUETOOTH interface. The aerosol-generating device 102 further comprises a power supply 126 and power and data interface ports 130.

The host device 101 includes a cavity 112 configured to host the aerosol-generating device 102 to recharge its power supply 126 via the power and interface ports 130. Preferably, the power supply 126 of the aerosol-generating device 102 may be designed to supply sufficient power for a one smoking experience, such that the user after consumption of a heat stick 104 has to re-insert the aerosol-generating device 102 into the host device 101 to recharge its battery 126 via the power and data interface ports 110 of the host device 101. The host device 101 further comprises a power supply 109.

The host device 101 includes a controller 108 comprising one or more processors and associated with a communication interface unit 106, which interacts with the controller 128 of the aerosol-generating device 102 to exchange/store data related to diagnostics, issue commands related to self-diagnostic procedures, exchange messages related to self-diagnostic procedures, etc. when the aerosol-generating device 102 and the host devices 101 are electrically coupled (for example, when the aerosol-generating device 102 is docked, via wireless communication, etc.). The communication interface unit 106, in turn, may be configured to exchange self-diagnostics data to/from the user interface device 201. Advantageously, communication interface unit 106 has a wireless communication module, preferably comprising a BLUETOOTH interface, which is a low power interface.

As shown, each of the aerosol-generating device 102 and the host device 101 includes a plurality of user-selectable switches 152-1, 152-2 and a plurality of indicators 162-1, 162-2, 162-3, 162-4, 162-5. The user-selectable switches 152-1, 152-2 may be selectable (for example, depressible) by a user as is indicated by the dashed lined arrows. As described herein, the user-selectable switches 152-1, 152-2 may be selectable to, among other things, initiate self-diagnostics of one or both of the aerosol-generating device 102 and the host device 101. For example, if the aerosol-generating device 102 is docked in the cavity 112 of the host device 101, initiation of the self-diagnostic procedure using the user-selectable switches 152-1, 152-2 of the host device 101 may perform, or execute, the self-diagnostic procedure on one or both of the aerosol-generating device 102 and the host device 101.

Although the aerosol-generating device 102 depicted in FIG. 1 includes a plurality of user-selectable switches 152-1, 152-2 and a plurality of indicators 162-1, 162-2, 162-3, 162-4, 162-5, the preferred embodiment of the aerosol-generating device 102 may only include a single user-selectable switch and a single indicator. The single user-selectable switch may be operable, for example, to "turn on" the aerosol-generating device 102. The single indicator may be operable, for example, to indicate whether the aerosol-generating device 102 is "on" or "off."

The plurality of indicators 162-1, 162-2, 162-3, 162-4, 162-5 may depict a light pattern indicative of, or showing, the diagnostic indication resulting from the self-diagnostic procedure. For example, some of the indicators 162-1, 162-2, 162-3, 162-4, 162-5 may light up a selected color, some of the indicators 162-1, 162-2, 162-3, 162-4, 162-5 may not light up (stay dark), and some of the indicators 162-1, 162-2, 162-3, 162-4, 162-5 may light up and blink.

Pattern examples 180, 181, 182, 183 of the indicators 162 of the illustrative host device 101 of FIG. 1 providing diagnostic indications related to the host device 101 are shown in FIG. 2, and pattern examples 185, 186, 187, 188, 189 of the indicators 162 of the illustrative host device 101 of FIG. 1 providing diagnostic indications related to the aerosol-generating device 102 are shown in FIG. 3. A key 179 is provided in these figures, which as shown, shows that each of the indicators 162-1, 162-2, 162-3, 162-4, 162-5 can provide, or display no light, white light, white blinking light, red light, and red blinking light.

The indicator 162-2 of the host device 101, when white, indicates that the host device 101 is in diagnostic mode. The indicator 162-2 is white in each example 180, 181, 182, 183, 185, 186, 187, 188, 189 of FIGS. 2-3, and thus, each example 180, 181, 182, 183, 185, 186, 187, 188, 189 depicts a pattern resulting from execution of a self-diagnostic procedure. In example 180, indicators 162-1, 162-5 are white, and this pattern may indicate that the host device 101 has no malfunction and has no need of replacement. In example 181, indicator 162-1 is white, indicator 162-2 is white and blinking, and indicator 162-5 is white and blinking, and this pattern may indicate that the host device 101 has no malfunction and has no need of replacement but is out of warranty. In example 182, indicator 162-1 is white and indicator 162-5 is red, and this pattern may indicate that the host device 101 is malfunctioning, is in need of replacement, and is within the warranty time period. In example 183, indicator 162-1 is white, indicator 162-2 is white and blinking, and indicator 162-5 is red and blinking, and this pattern may indicate that the host device 101 is malfunctioning, is in need of replacement, and is outside of the warranty time period.

When the aerosol-generating device 102 is received by the host device 101, self-diagnostics of the aerosol-generating device 102 may be performed and the indicators of the host device 101 may be used to show the diagnostic indication as shown in FIG. 3. In example 185, indicators 162-1 and 162-5 are white, and this pattern may indicate that the aerosol-generating device 102 has no malfunction and has no need of replacement. In example 186, indicator 162-1 is white and blinking and indicator 162-5 is white, and this pattern may indicate that the aerosol-generating device 102 has no malfunction and has no need of replacement but is out of warranty. In example 187, indicator 162-1 is red and indicator 162-5 is white, and this pattern may indicate that the aerosol-generating device 102 is malfunctioning, is in need of replacement, and is within the warranty time period. In example 188, indicator 162-1 is red and blinking and indicator 162-5 is white, and this pattern may indicate that the aerosol-generating device 102 is malfunctioning, is in need of replacement, and is outside of the warranty time period. In example 189, indicator 162-1 is not lit (dark) and indicator 162-5 is white, and this pattern may indicate that the aerosol-generating device 102 is not located in the host device 101 or not recognized by the host device 101.

Although the examples 180, 181, 182, 183, 185, 186, 187, 188, 189 of FIGS. 2-3 are patterns of indicators 162 of the host device 101, it is to be understood that the same or similar concepts may pertain or be used by the aerosol-generating device 102 if, for example, the aerosol-generating device 102 includes a plurality of indicators 162 as shown in FIG. 1.

An illustrative user interface device 201 including a display 206 depicting a graphical user interface 250 is shown in FIG. 4. The graphical user interface 250 includes a graphical region 251 for the initiation of a diagnostic process. A user may select the graphical region 251, which in turn, may wirelessly transmit a self-diagnostic message to the aerosol-generating apparatus 100. The graphical user interface 250 further includes a diagnosis area 252 depicting a diagnostic code ("CO2") resulting the initiated self-diagnostic process and a textual description of the diagnostic code ("Damaged or Broken Heating Blade"), a remedy area 253 depicting a textual description of a remedy for the diagnostic code ("Replace Aerosol-Generating Device"), and a warranty area 254 depicting a textual description of a warranty status for the aerosol-generating device ("Out of Warranty").

The invention claimed is:

1. An aerosol-generating apparatus comprising:
   a controller comprising one or more processors, the controller configured to:
      allow a user to initiate diagnostics by at least one of:
         initiating the diagnostics of aerosol-generating apparatus in response to user selection of a user-selectable switch included in the aerosol-generating apparatus; and
         receiving a diagnostic initiation message from a user interface device separate from the aerosol-generating apparatus;
      perform a self-diagnostic procedure of the aerosol-generating apparatus in response to initiation of diagnostics by the user; and
      provide a diagnostic indication to the user based on at least the self-diagnostic procedure.

2. The aerosol-generating apparatus of claim 1, wherein the aerosol-generating apparatus comprises:
   an aerosol-generating device to use an aerosol generating article to generate aerosol, the aerosol-generating device comprising a power supply; and
   a host device comprises an interface to be operably coupled to the aerosol-generating device to at least recharge the power supply of the aerosol-generating device, wherein the host device comprises the controller and the user-selectable switch to allow the user to initiate diagnostics.

3. The aerosol-generating apparatus of claim 1, wherein the aerosol-generating apparatus comprises an aerosol-generating device to use an aerosol generating article to generate aerosol, wherein the aerosol-generating device comprises the controller and the user-selectable switch to allow the user to initiate diagnostics.

4. The aerosol-generating apparatus of claim 2, wherein one or both of the host device and the aerosol-generating apparatus further comprises at least one indicator to display the diagnostic indication to the user.

5. The aerosol-generating apparatus of claim 4, wherein the at least one indicator is configured to one or more of blink a selected pattern and depict a selected color to display the diagnostic indication to the user.

6. The aerosol-generating apparatus of claim 1, wherein initiating the diagnostics of aerosol-generating apparatus in response to user selection of the user-selectable switch included in the aerosol-generating apparatus comprises initiating the diagnostics of aerosol-generating apparatus in response to user selection of the user-selectable switch according to a selected pattern.

7. The aerosol-generating apparatus of claim 1, wherein the user-selectable switch comprises a depressible button.

8. The aerosol-generating apparatus of claim 1, wherein providing a diagnostic indication to the user based on at least the self-diagnostic procedure comprises displaying the diagnostic indication to the user on a graphical user interface of the user interface device.

9. The aerosol-generating apparatus of claim 1, wherein the user interface device comprises a cellular telephone.

10. The aerosol-generating apparatus of claim 1, wherein the controller is further configured to execute:
    providing a diagnosis mode indication to the user to indicate that the aerosol-generating apparatus is configured in diagnosis mode in response to initiation of diagnostics of aerosol-generating apparatus by the user.

11. The aerosol-generating apparatus of claim 1, wherein the diagnostic indication to the user is indicative of physical damage to the aerosol-generating apparatus.

12. The aerosol-generating apparatus of claim 11, wherein the physical damage to the aerosol-generating apparatus is a broken heater blade of an aerosol-generating device of the aerosol-generating apparatus.

13. The aerosol-generating apparatus of claim 1, wherein the diagnostic indication to the user is indicative of improper usage of the aerosol-generating apparatus.

14. The aerosol-generating apparatus of claim 1, wherein the controller is further configured to execute:
    determining whether the aerosol-generating apparatus is in a warranty period,
    wherein the diagnostic indication to the user is indicative of whether the aerosol-generating apparatus should be replaced and is within or outside of the warranty period.

15. A method for use with an aerosol-generating apparatus comprising:
    allowing a user to initiate diagnostics of an aerosol-generating apparatus by at least one of:
    initiating the diagnostics of aerosol-generating apparatus in response to user selection of a user-selectable switch included in the aerosol-generating apparatus; and
    receiving a diagnostic initiation message from a user interface device separate from the aerosol-generating apparatus;

performing a self-diagnostic procedure of the aerosol-generating apparatus in response to initiation of diagnostics of aerosol-generating apparatus by the user; and providing a diagnostic indication to the user based on at least the self-diagnostic procedure.

16. The method of claim 15, wherein the aerosol-generating apparatus comprises:
an aerosol-generating device to use an aerosol generating article to generate aerosol, the aerosol-generating device comprising a power supply; and
a host device comprises an interface to be operably coupled to the aerosol-generating device to at least recharge the power supply of the aerosol-generating device, wherein the host device comprises the user-selectable switch to allow the user to initiate diagnostics.

17. The method of claim 15, wherein the aerosol-generating apparatus comprises an aerosol-generating device to use an aerosol generating article to generate aerosol, wherein the aerosol-generating device comprises the user-selectable switch to allow the user to initiate diagnostics.

18. The method of claim 16, wherein one or both of the host device and the aerosol-generating apparatus further comprises at least one indicator to display the diagnostic indication to the user.

19. The method of claim 18, wherein the at least one indicator is configured to one or more of blink a selected pattern and depict a selected color to display the diagnostic indication to the user.

20. The method of claim 15, wherein initiating the diagnostics of aerosol-generating apparatus in response to user selection of the user-selectable switch included in the aerosol-generating apparatus comprises initiating the diagnostics of aerosol-generating apparatus in response to user selection of the user-selectable switch according to a selected pattern.

21. The method of claim 15, wherein the user-selectable switch comprises a depressible button.

22. The method of claim 15, wherein providing a diagnostic indication to the user based on at least the self-diagnostic procedure comprises displaying the diagnostic indication to the user on a graphical user interface of the user interface device.

23. The method of claim 15, wherein the user interface device comprises a cellular telephone.

24. The method of claim 15, wherein the method further comprises:
providing a diagnosis mode indication to the user to indicate that the aerosol-generating apparatus is configured in diagnosis mode in response to initiation of diagnostics of aerosol-generating apparatus by the user.

25. The method of claim 15, wherein the diagnostic indication to the user is indicative of physical damage to the aerosol-generating apparatus.

26. The method of claim 25, wherein the physical damage to the aerosol-generating apparatus is a broken heater blade of an aerosol-generating device of the aerosol-generating apparatus.

27. The method of claim 15, wherein the diagnostic indication to the user is indicative of improper usage of the aerosol-generating apparatus.

28. The method of claim 15, wherein the method further comprises:
determining whether the aerosol-generating apparatus is in a warranty period,
wherein the diagnostic indication to the user is indicative of whether the aerosol-generating apparatus should be replaced and is within or outside of the warranty period.

29. Computer program product for use with aerosol-generating apparatus comprising a non-transitory computer readable medium having program code stored thereon, the program code configured, when said computer program product is run on a computer, to:
allow a user to initiate diagnostics of an aerosol-generating apparatus by at least one of:
initiating the diagnostics of aerosol-generating apparatus in response to user selection of a user-selectable switch included in the aerosol-generating apparatus; and
receiving a diagnostic initiation message from a user interface device separate from the aerosol-generating apparatus;
perform a self-diagnostic procedure of the aerosol-generating apparatus in response to initiation of diagnostics of aerosol-generating apparatus by the user; and
provide a diagnostic indication to the user based on at least the self-diagnostic procedure.

* * * * *